(12) United States Patent
Wegelin et al.

(10) Patent No.: US 9,728,070 B2
(45) Date of Patent: Aug. 8, 2017

(54) PORTABLE COMPLIANCE DISPENSER

(71) Applicant: GOJO Industries, Inc., Akron, OH (US)

(72) Inventors: Jackson W. Wegelin, Stow, OH (US); Matthew J. Archer, Aurora, OH (US)

(73) Assignee: GOJO Industries, Inc., Akron, OH (US)

( * ) Notice: Subject to any disclaimer, the term of this patent is extended or adjusted under 35 U.S.C. 154(b) by 6 days.

(21) Appl. No.: 14/982,169

(22) Filed: Dec. 29, 2015

(65) Prior Publication Data
US 2016/0110989 A1    Apr. 21, 2016

Related U.S. Application Data

(62) Division of application No. 13/095,052, filed on Apr. 27, 2011, now Pat. No. 9,262,905.

(51) Int. Cl.
*G08B 23/00*    (2006.01)
*G08B 21/24*    (2006.01)
*A61L 2/00*    (2006.01)
*A61L 2/24*    (2006.01)

(52) U.S. Cl.
CPC .......... *G08B 21/245* (2013.01); *A61L 2/0088* (2013.01); *A61L 2/24* (2013.01); *A61L 2202/14* (2013.01); *A61L 2202/16* (2013.01)

(58) Field of Classification Search
CPC .............. G08B 21/245; A61L 2202/14; A61L 2202/16; A61L 2/0088; A61L 2/24
See application file for complete search history.

(56) References Cited

U.S. PATENT DOCUMENTS

| | | | |
|---|---|---|---|
| 2010/0094581 A1* | 4/2010 | Cagle | G08B 21/245 702/127 |
| 2010/0169111 A1* | 7/2010 | Brue | G06Q 50/22 705/2 |
| 2010/0206976 A1* | 8/2010 | Salentine | A45F 5/004 242/379.2 |
| 2011/0054285 A1* | 3/2011 | Searle | A61M 5/14244 600/365 |
| 2011/0154889 A1* | 6/2011 | Stafford | G01N 33/48778 73/61.59 |
| 2011/0234598 A1* | 9/2011 | Scarola | G08B 21/245 345/440.1 |

* cited by examiner

*Primary Examiner* — George Bugg
*Assistant Examiner* — Renee Dorsey
(74) *Attorney, Agent, or Firm* — Cooper Legal Group, LLC

(57) ABSTRACT

A portable compliance dispenser provides a compliance module that is removably attached to a replaceable refill container, which carries any suitable liquid material, such as sanitizer. The compliance module is configured to be worn or carried by an individual and communicates hygiene compliance data to a remote monitoring station when material from the refill container is dispensed.

8 Claims, 17 Drawing Sheets

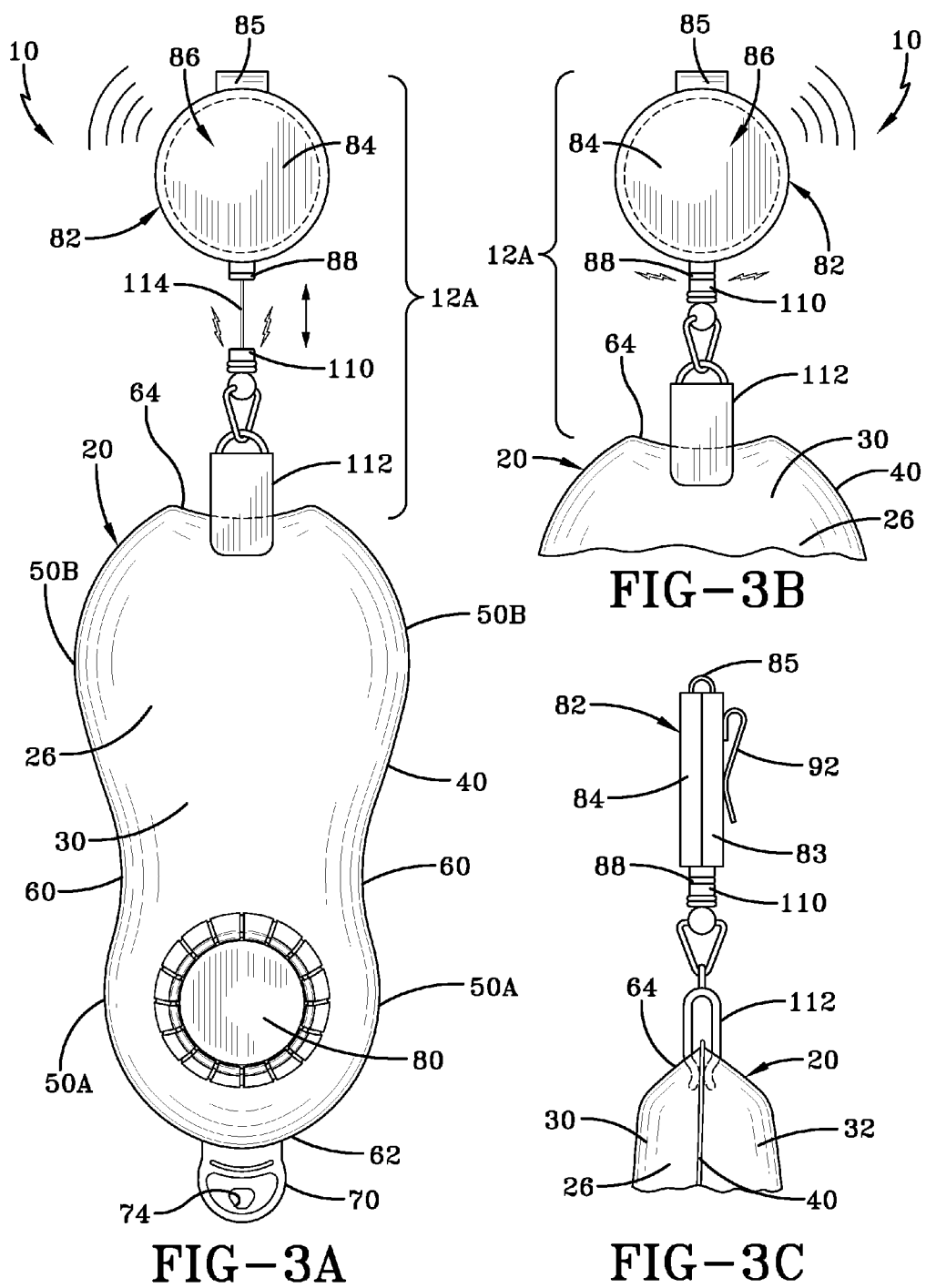

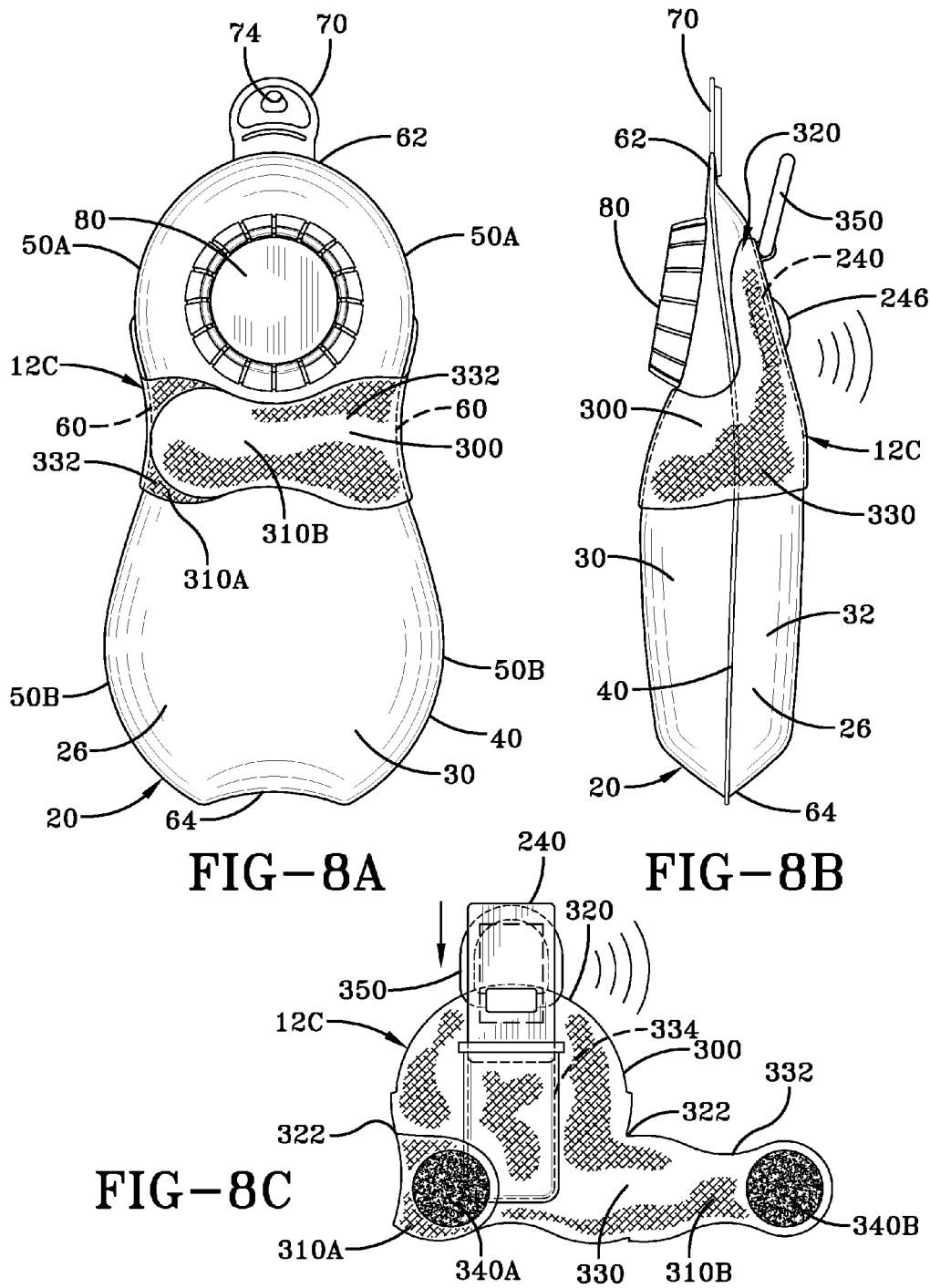

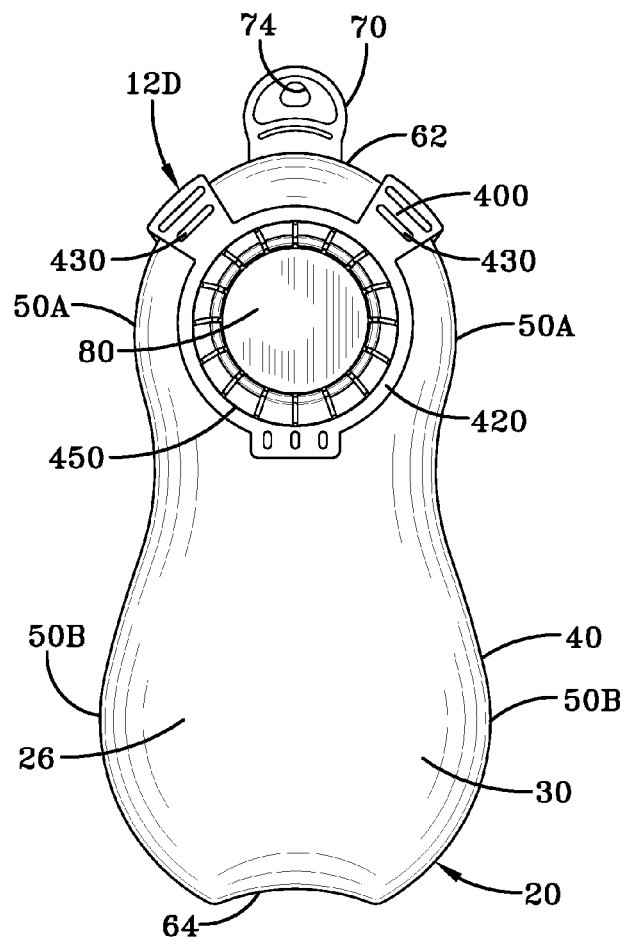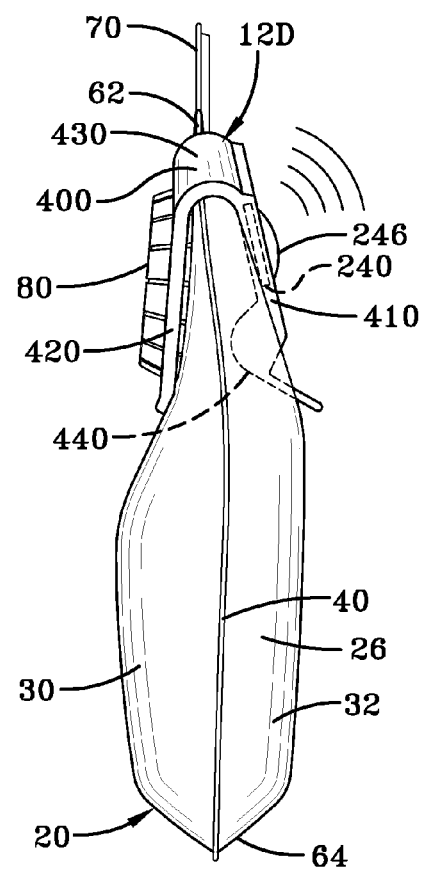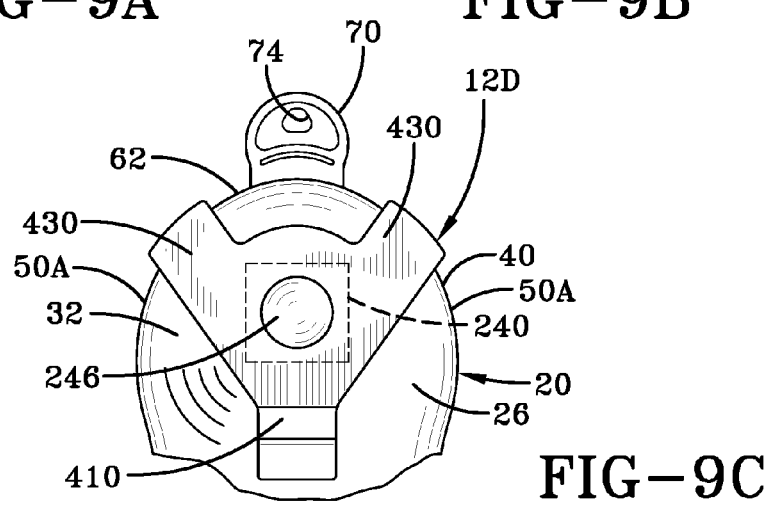

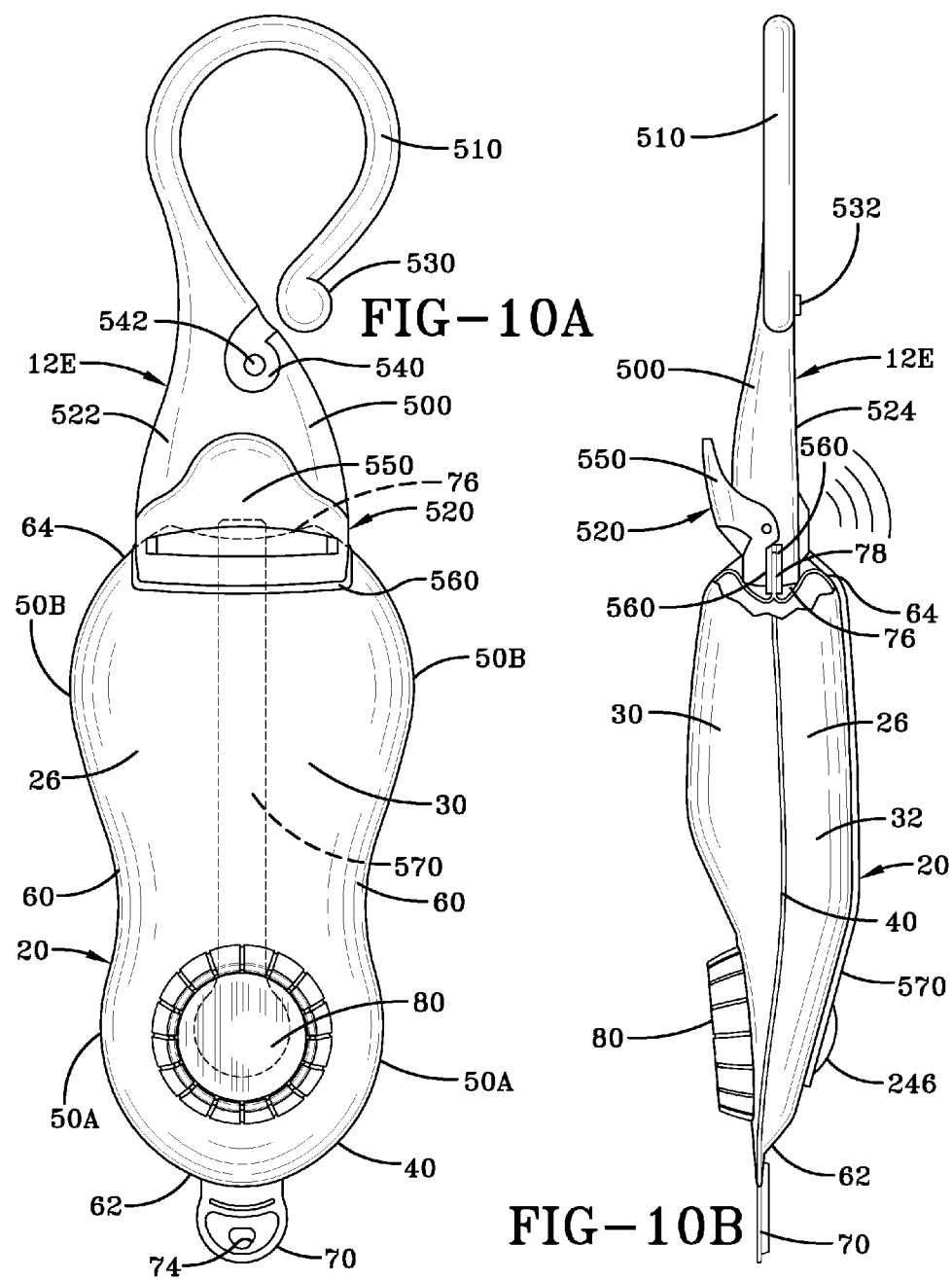

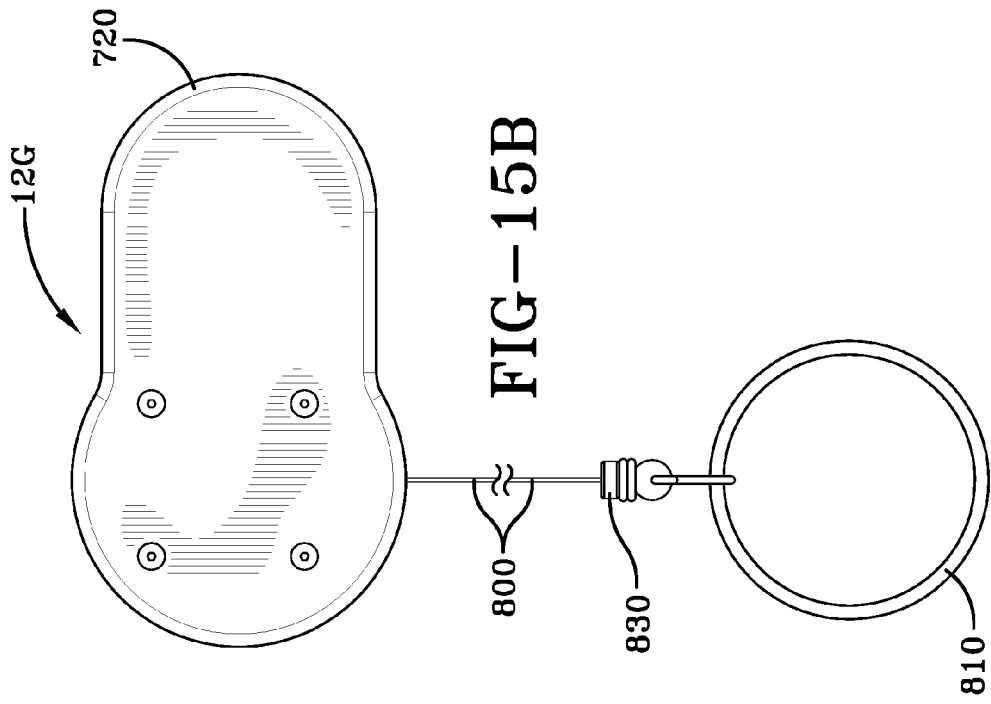
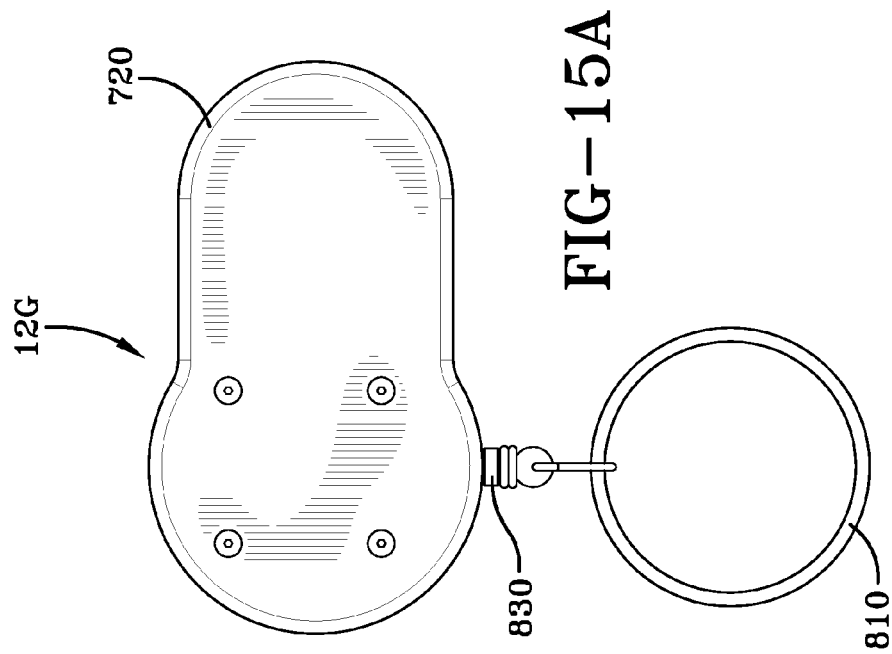

PORTABLE COMPLIANCE DISPENSER

CROSS-REFERENCE TO RELATED APPLICATION

This application is a divisional of U.S. patent application Ser. No. 13/095,052, filed on Apr. 27, 2011, the contents of which are incorporated herein by reference.

TECHNICAL FIELD

The present invention generally relates to dispensers, such as sanitizer dispensers. In particular, the present invention relates to portable dispensers capable of collecting hygiene compliance data. More particularly, the present invention relates to portable dispensers that collect and transmit hygiene compliance data to a remote monitoring station.

BACKGROUND OF THE INVENTION

Recently, the public has become increasingly concerned with disease and its transmission, and as such, there is an increased awareness of the importance of hand cleansing and hygiene in general. For example, with respect to the transmission of E. coli in the food services industry, the rhinovirus in elementary schools, and nosocomial diseases within healthcare facilities, numerous studies have cited hand hygiene as an effective measure to guard against disease transmission. In response, health care, food service, and hotel and travel industries have been forced to examine their hygiene protocols and procedures to ensure that their personnel are adopting habits that are efficacious in the prevention of disease transmission.

In order to minimize the possibility of the transmission of bacteria or viruses by hand washing, full compliance with hand washing hygiene standards must be observed, as the failure of one individual to properly sanitize his or her hands can negate the efforts of others who come in contact with such individual. Thus, to ensure employees or other individuals have sufficient access to sanitizer, the current trend has been to permanently install full-size dispensers at designated areas throughout a building or work area. Such dispensers are rigidly affixed to a wall or counter and are capable of being refilled with sanitizer when they are emptied.

Unfortunately, such full-size fixed dispensers require that users return to them each time they are in need of sanitizer, which is inconvenient as users generally require multiple sanitizer applications throughout the day. Also, if the user is required to travel out of his or her way to obtain the sanitizer from the fixed dispenser, then he or she may be less inclined to sanitize their hands in accordance with predetermined hygiene protocols. In addition, installation of a sufficient quantity of fixed sanitizer dispensers to provide complete coverage throughout a facility, such as a hospital, would require a substantial cost. Moreover, in such a circumstance where there is a substantial number of full-size, fixed dispensers installed, an employee must periodically refill the sanitizer dispensers, which is costly and time consuming.

Alternatively, while portable dispensers are available, they are inconvenient to refill with liquid material, such as soap or sanitizer. In addition, such portable dispenser devices fail to acquire hygiene compliance data, which is desirable.

Therefore, there is a need for a portable compliance dispenser that is worn or carried by a user. In addition, there is a need for a portable compliance dispenser that is able to dispense liquid material, such as sanitizer, that collects and transmits hygiene compliance data to a remote monitoring station. Still yet, there is a need for a portable compliance monitor that dispenses liquid material, such as sanitizer, from a replaceable refill container.

SUMMARY OF THE INVENTION

In light of the foregoing, it is a first aspect of the present invention to provide a portable compliance module to monitor the use of a refill container to communicate hygiene compliance data to a compliance monitor when material is dispensed from the refill container, the portable compliance module comprising a controller; a transmitter coupled to said controller; a magnetic switch coupled to said controller; an attachment clip adapted to be attached to the refill container; a container magnet attached to said attachment clip, said magnetic switch configured to detect the presence of said container magnet; and a retractable tether coupled to said magnetic switch and to said container magnet; wherein said transmitter transmits a wireless compliance signal to the compliance monitor when the presence of said container magnet is not detected by said magnetic switch to indicate completion of a dispensing event, said transmitter ceasing transmission of said wireless compliance signal when said container magnet is detected by said magnetic switch.

It is a further aspect of the present invention to provide a portable compliance dispenser configured to communicate hygiene compliance data to a remote compliance monitor comprising a refill container having a pump element to dispense material therefrom when actuated and a compliance module comprising a stretchable sleeve adapted to receive at least part of said refill container therein; and a communication module having a control actuator carried by said sleeve; wherein when said control actuator is actuated, said communication module transmits compliance data to the remote compliance monitor.

It is another aspect of the present invention to provide a portable hygiene compliance dispenser configured to communicate hygiene compliance data to a remote compliance monitor comprising a refill container having a pump element to dispense material therefrom when actuated and a compliance module comprising a body from which extends a pair of attachment arms, wherein said arms are disposed about said refill container and removably attached to each other to retain said compliance module to said refill container; and a communication module having a control actuator carried by said body; wherein when said control actuator is actuated, said communication module transmits compliance data to the remote compliance monitor.

Yet a further aspect of the present invention is to provide a portable hygiene compliance dispenser configured to communicate hygiene compliance data to a remote compliance monitor comprising a refill container having a pump element to dispense material therefrom when actuated and a compliance module comprising a body having a retention arm that is coupled to a retention ring by at least one coupling arch, wherein said retention ring is configured to receive said pump element of said refill container therethrough, said retention arm and said retention ring apply a compressive force to said refill container to retain said compliance module to said refill container; and a communication module having a control actuator carried by said body; wherein when said control actuator is actuated, said communication module transmits compliance data to the remote compliance monitor.

It is another aspect of the present invention to provide a portable hygiene compliance dispenser configured to communicate hygiene compliance data to a remote compliance monitor comprising a refill container having an edge from which extends an attachment section, said refill container having a pump element to dispense material therefrom when actuated; and a compliance module comprising a body from which extends a hook and an attachment clamp, said clamp being removably attached to said attachment section of said refill container; a communication module disposed within said body; and an extension section extending from said body that carries a control actuator that is coupled to said communication module to a position substantially aligned with said pump element; wherein when said control actuator is actuated, said communication module transmits a compliance signal to the remote compliance monitor.

Yet a further aspect of the present invention is to provide a portable hygiene compliance dispenser configured to communicate hygiene compliance data to a remote compliance monitor comprising a refill container having a pump element to dispense material therefrom when actuated, and a compliance module comprising a body that includes an attachment clip, and a pivotably attached mounting clip, said mounting clip configured to be removably attached to said refill container; and a communication module having a control actuator disposed within said mounting clip; wherein when said control actuator is actuated, said communication module transmits compliance data to the remote compliance monitor.

Still another aspect of the present invention is to provide a portable compliance module to monitor the use of a dispensing container having a pump extending through a collar, so as to communicate hygiene compliance data to a compliance monitor when material is dispensed from the dispensing container, the portable compliance module comprising a controller; a transmitter coupled to said controller; a magnetic switch coupled to said controller; a retainer adapted to be attached adjacent to the collar edge; a container magnet attached to said retainer, said magnetic switch configured to detect the presence of said container magnet; and a retractable tether coupled to said magnetic switch and to said container magnet; wherein said transmitter transmits a wireless compliance signal to the compliance monitor when the presence of said container magnet is not detected by said magnetic switch to indicate completion of a dispensing event, said transmitter ceasing transmission of said wireless compliance signal when said container magnet is detected by said magnetic switch.

BRIEF DESCRIPTION OF THE DRAWINGS

These and other features and advantages of the present invention will become better understood with regard to the following description, appended claims, and accompanying drawings where:

FIG. 3A is an elevational view of one embodiment of a portable compliance dispenser showing the refill container separated from a compliance module in accordance with the concepts of the present invention;

FIG. 3B is a partial elevational view of the portable compliance module of FIG. 3A showing the refill container magnetically coupled to the compliance module in accordance with the concepts of the present invention;

FIG. 3C is a side elevational view of the portable compliance module of FIG. 3A in accordance with the concepts of the present invention;

FIG. 8A is an elevational view of an alternate portable compliance dispenser retained to the refill container by a fabric body in accordance with the concepts of the present invention;

FIG. 8B is a side elevational view of the portable compliance dispenser of FIG. 8A in accordance with the concepts of the present invention;

FIG. 8C is an elevational view of the portable compliance dispenser of FIG. 8A showing the retention arms used to attach the compliance module to the refill container in accordance with the concepts of the present invention;

FIG. 9A is an elevational view of another embodiment of the portable compliance dispenser having a compliance module that comprises a clip that is retained to the refill container in accordance with the concepts of the present invention;

FIG. 9B is a side elevational view of the portable compliance dispenser of FIG. 9A in accordance with the concepts of the present invention;

FIG. 9C is an elevational view of the clip used to retain the compliance module of FIG. 9A to the refill container in accordance with the concepts of the present invention;

FIG. 10A is an elevational view of an alternate portable compliance dispenser having a compliance module that is attached to the refill container by a clip in accordance with the concepts of the present invention;

FIG. 10B is a side elevational view showing the portable compliance dispenser of FIG. 10A in accordance with the concepts of the present invention;

FIG. 15A is an elevational view of the portable compliance dispenser of FIG. 12 showing the tether in a retracted position in accordance with the concepts of the present invention; and FIG. 15B is an elevational view of the portable compliance dispenser of FIG. 12 showing a tether in an extended position in accordance with the concepts of the present invention.

DETAILED DESCRIPTION OF THE INVENTION

Figure 1:
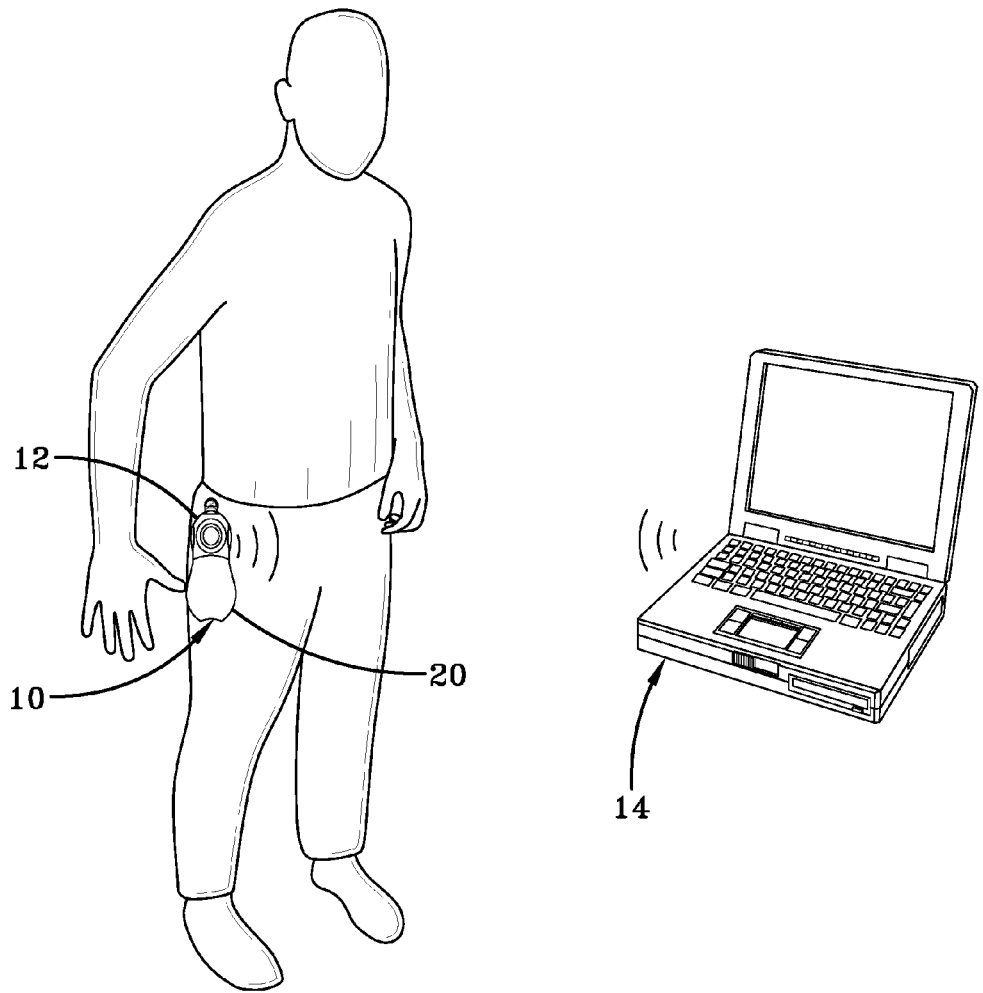
FIG. 1 is a perspective view showing a portable compliance dispenser in communication with a remote monitoring station in accordance with the concepts of the present invention.

A portable compliance dispenser that is wearable by an individual is generally referred to by the numeral 10, as shown in FIG. 1 of the drawings. The dispenser 10 comprises a compliance module 12 that wirelessly communicates hygiene compliance data with a remote monitoring station or compliance monitor 14 when liquid material, such as sanitizer, is dispensed from a refill container 20 that is operatively coupled to the module 12. Thus, the portable compliance dispenser 10 provides a manner in which liquid material, such as sanitizer, can be portably dispensed from a replaceable refill container while collecting and communicating hygiene compliance data associated with its usage.

Figures 2A, 2B:
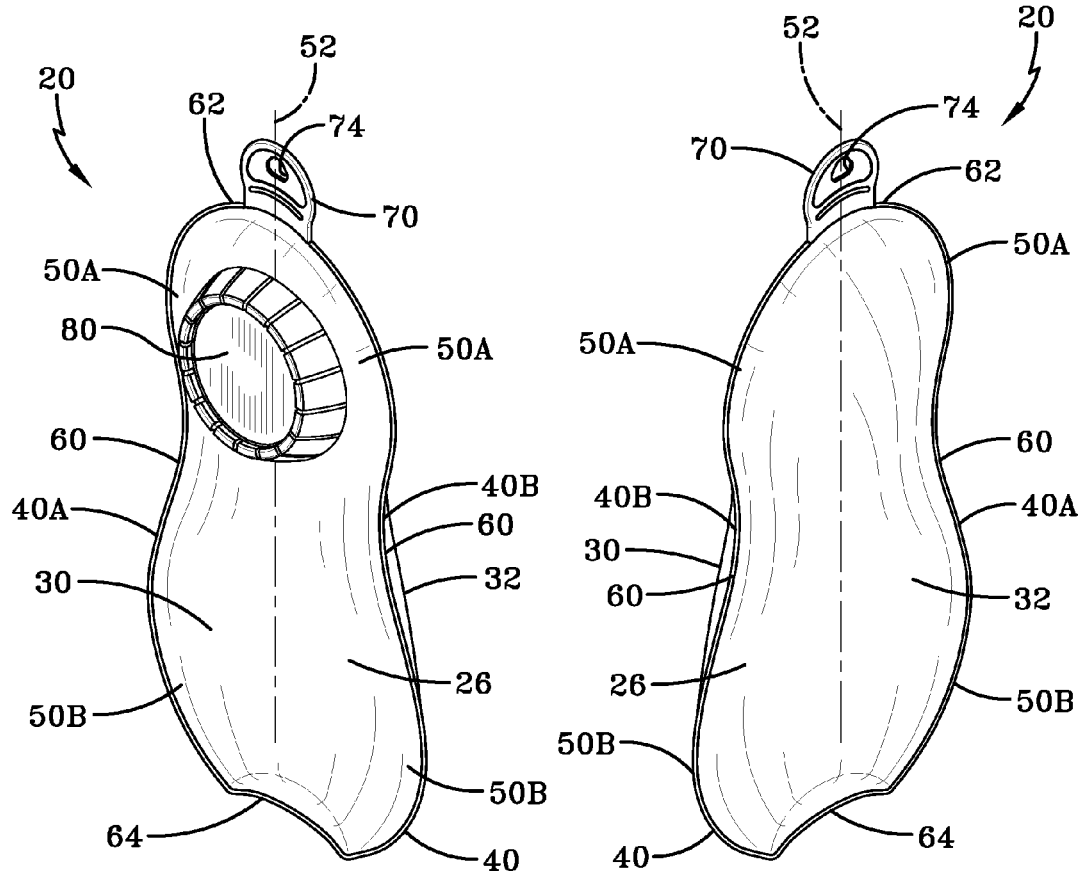
FIG. 2A is a perspective view of a front section of a refill container used by the portable compliance dispenser that contains liquid material to be dispensed in accordance with the concepts of the present invention.
FIG. 2B is a perspective view of a rear section of the refill container in accordance with the concepts of the present invention.
Figure 2C:
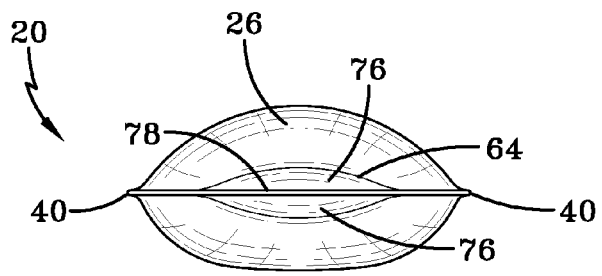
FIG. 2C is a bottom plan view of the attachment end of the refill container in accordance with the concepts of the present invention.
Figure 4:
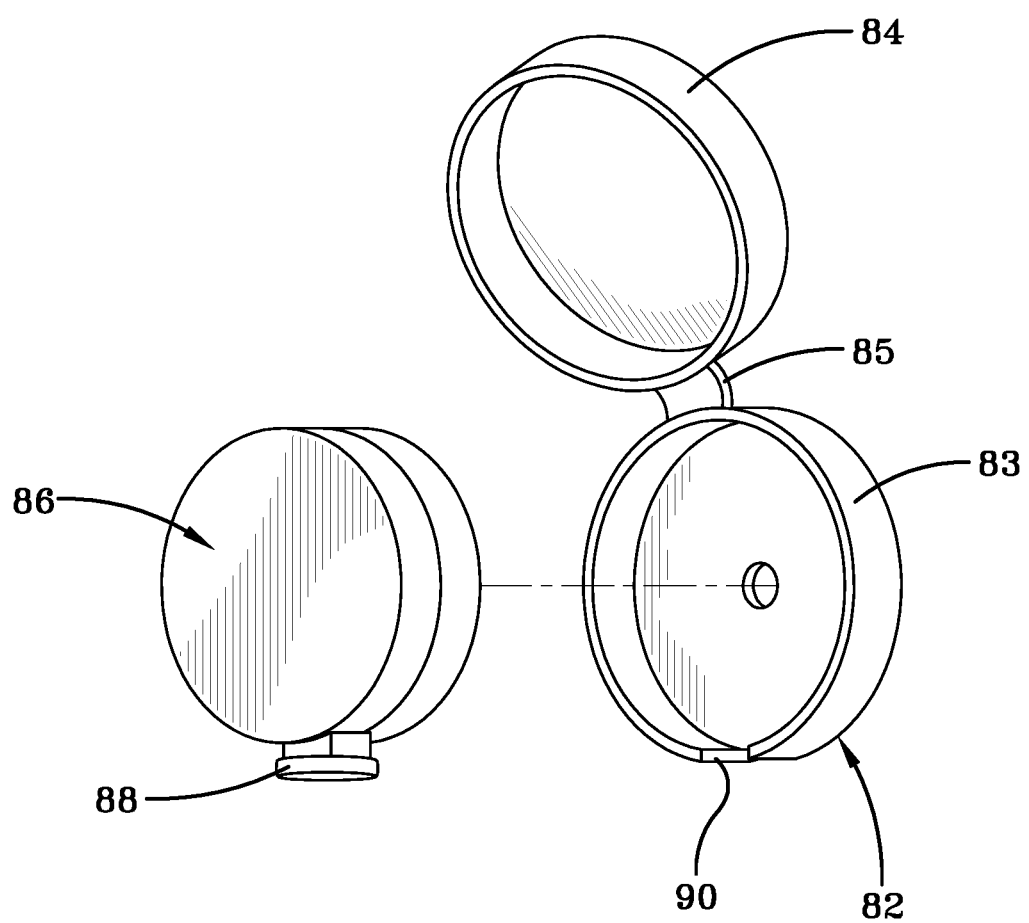
FIG. 4 is a perspective view of a communication module removably retained in a carrying case provided by the compliance module shown in FIG. 3A in accordance with the concepts of the present invention.

Specifically, the portable compliance dispenser 10 comprises a plurality of compliance modules 12, which are designated by identifiers A-G. Specifically, the compliance modules 12A-F are configured for attachment with the refill container 20 shown in FIGS. 2A-C, while compliance module 12G is configured for attachment to a dispensing container to be discussed below. The refill container 20 is configured as a modular unit and is able to carry an amount of any liquid material, such as soap, sanitizer, or moisturizer for example. Specifically, the refill container 20 comprises an elongated body 26 formed of any suitable material, such as plastic, and has opposed front and rear sections 30 and 32, which are joined about an edge 40 having opposed lateral portions 40A and 40B. The lateral portions 40A-B of the edge 40 are defined by two pairs of substantially rounded or curved shoulder sections 50A and 50B, which extend away from a central midline 52 of the refill container 20. The pairs of shoulders 50A and 50B are spaced apart along the midline 52 to form a waist 60 in the region therebetween that is approximately in the middle of the refill container 20. The refill container 20 includes a dispensing end 62 that is proximate to the shoulders 50A, and an opposed attachment end 64 that is proximate to the shoulders 50B. Extending from the edge 40 of the refill container 20 at the dispensing end 62 is a tab 70 that includes a dispensing port 74 that is in fluid connection with the liquid material contained in the refill container 20. The attachment end 64 of the refill container 20 includes a cavity 76, as shown in FIG. 2C, with a substantially planar attachment section 78 extending from the edge 40. The front section 30 of the refill container 20 also includes a pump element, such as dome pump 80 that when compressed by a user's hand or fingers, generates the necessary pressure to force the liquid material out of the dispensing port 74, thereby dispensing the liquid material to the user. As such, the shape and configuration of the refill container 20 is modular, allowing it to be compatible with the various compliance modules 12A-F that are discussed in detail below. In one aspect, the refill container 20 may comprise a pouch, for example.

In one embodiment of the portable compliance dispenser 10, a compliance module 12A is shown in FIGS. 3A-C and 4. Specifically, the compliance module 12A comprises a carrying case 82, shown clearly in FIG. 4, which includes a base 83 that is pivotably attached to a lid 84 by a hinge 85, such as a living hinge. The base 83 is configured to house and retain a communication module 86, which includes a magnetic switch 88 that is dimensioned to be received within a notch 90 disposed in the periphery of the base 83. As such, when the module 86 is disposed within the base 83, the lid 84 may be closed and retained to the base 83 using any suitable means, such as a snap, latch, or the like. The case 82 also includes a carrying clip 92 that is suitable for removably attaching the case 82 to the user. The magnetic switch 88 is configured to detect the proximity of the container magnet 110 that is carried by or otherwise attached to an attachment clip 112 that is attached (or removably attached) to the refill container 20. It should be appreciated that the attachment clip 112 may be coupled to the refill container 20 using any suitable means of fixation, including compressive attachment or adhesive for example. Furthermore, the magnetic switch 88 and the container magnet 110 are joined by a retractable tether 114, which may comprise any suitable cable, cord, line, or the like, or alternatively, the tether 114 may comprise an elastic cord or band that is configured to elastically urge the container magnet 110 and the magnetic switch 88 together. In other words when the compliance module 12A is in use, the tether 114 serves to normally urge the container magnet 110, as well as the refill container 20, to be proximate to the communication module 86 such that the magnetic switch 88 detects the presence of the container magnet 110. Alternatively, when the refill container 20 is to be used, the tether 114 allows the refill container 20 and container magnet 110 to be pulled or moved away from or outside of the magnetic detection range of the magnetic switch 88.

Figure 5:
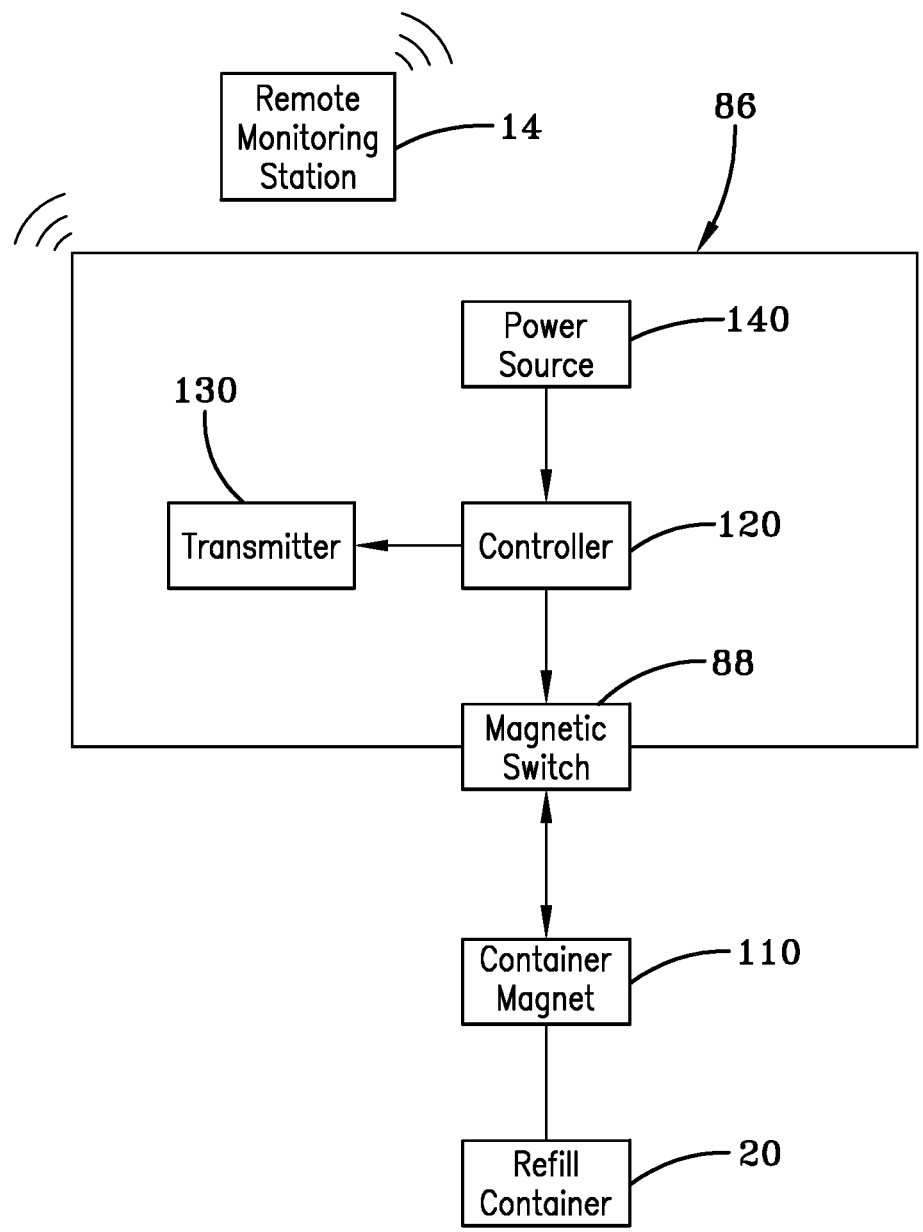
FIG. 5 is a block diagram of the communication module utilized by the portable compliance dispenser shown in FIGS. 3A-C in accordance with the concepts of the present invention.

The communication module 86, shown in FIG. 5, comprises a controller 120 that includes the necessary hardware and/or software to carryout the functions to be discussed. Coupled to the controller 120 is a wireless transmitter 130 that is configured to transmit or otherwise communicate wireless signals, such as a hygiene compliance signal, that contain hygiene compliance data to the remote monitoring station 14 in a manner to be discussed. In one aspect, the transmitter 130 may be replaced with a transceiver that is capable of transmitting and receiving data to and from the remote monitoring station 14. The magnetic switch 88 is coupled to the controller 120, which is configured to detect the presence and non-presence of the container magnet 110, as previously discussed. Moreover, the controller 120 and the transmitter 130 are powered by a power source 140, such as a battery or solar cell for example.

The remote monitoring station 14 that is used to communicate with the compliance module 12A, as well as compliance modules 12B-G to be discussed, comprises any suitable computing system that is configured to receive the wireless hygiene compliance signal and data sent from the compliance modules 12A-G. In one aspect, the remote monitoring station 14 may include input and output devices, such as a keyboard, mouse, and monitor. This allows users of the monitoring station 14 to analyze and process the received hygiene compliance data to determine if individuals wearing the compliance modules 12A-G are in compliance with predetermined hygiene standards and protocols.

Thus, during operation of compliance module 12A, the tether 114 is in a normally retracted state such that the container magnet 110 is within the detection range of the container magnet 110. As such, when the container magnet 110 is moved out of the detection range of the magnetic switch 88 by extending the tether 114 in order to dispense material from the refill container 20, the compliance module 12A transmits a wireless hygiene compliance signal or compliance data to the remote monitoring station 14 via the transmitter 130 to indicate that the refill container 20 is being used and that a hygiene compliance and dispensing event has occurred. That is, the remote monitoring station 14 identifies the transmission of the hygiene compliance signal or compliance data and records it as a completion of a hygiene compliance event, signifying that liquid material in the refill container 20 has been dispensed from the dispensing port 74 by the user of the dispenser 10 by depression of the dome pump 80. After the dispensing event has been completed and the tether 114 is retracted such that the presence of the container magnet 110 is detected by the magnetic switch 88, the transmitter 130 is disabled so that it does not transmit the compliance signal or data.

It should be appreciated that each compliance module 12A may be assigned a unique identification code that is associated with transmitted hygiene compliance signal and data sent to the remote monitoring station 14. This allows an administrator of the monitoring station 14 to identify and discretely monitor one or more users wearing the compliance module 12A to determine if he or she is in compliance with predetermined hygiene standards and protocols, based on the collected hygiene compliance data.

Figure 6A:
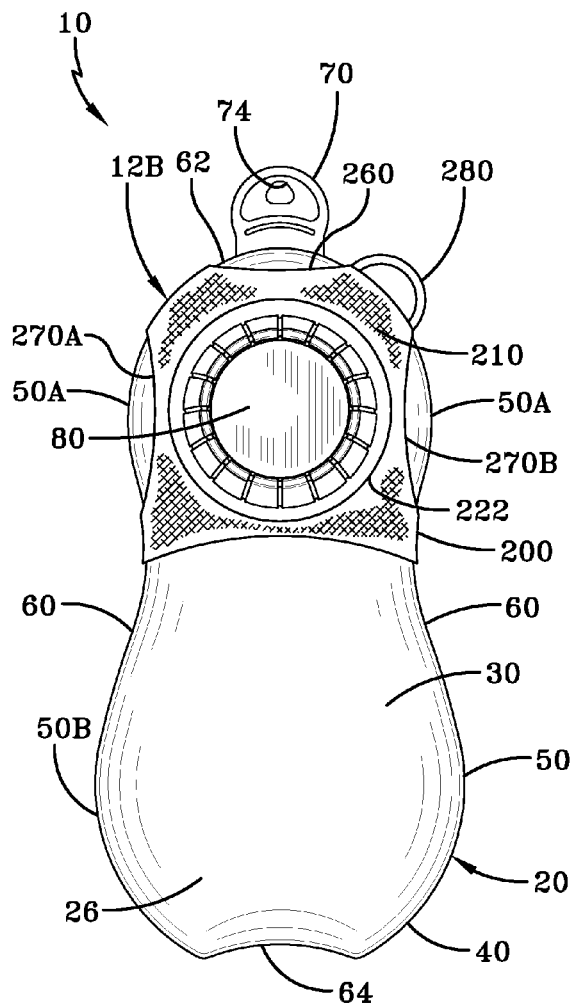
FIG. 6A is a front elevational view of an alternate portable compliance dispenser in which a compliance module comprises a stretchable sleeve that is attached to the refill container in accordance with the concepts of the present invention.
Figure 6B:
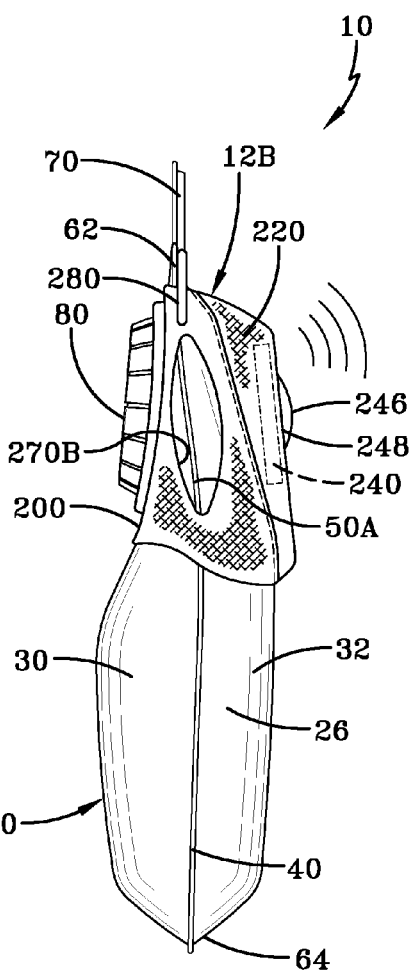
FIG. 6B is a side elevational view of the portable compliance dispenser of FIG. 6A in accordance with the concepts of the present invention.

In another embodiment of the portable compliance dispenser 10, a compliance module 12B for use with the refill container 20 is shown in FIGS. 6A-B. The compliance module 12B comprises a sleeve 200, which may be formed from any suitable material, such as fabric, as well as stretchable material including latex, neoprene, or the like. The sleeve 200 includes opposed front and rear sections 210 and 220 that form a cavity to receive the refill container 20 therein. As such, when the sleeve 200 is installed, the front section 210 of the sleeve 200 is configured to be disposed adjacent to the front section 20 of the refill container 20, such that the dome pump 80 of the refill container 20 is received through a receiving aperture 222 provided by the front section 210 of sleeve 200.

Figure 7:
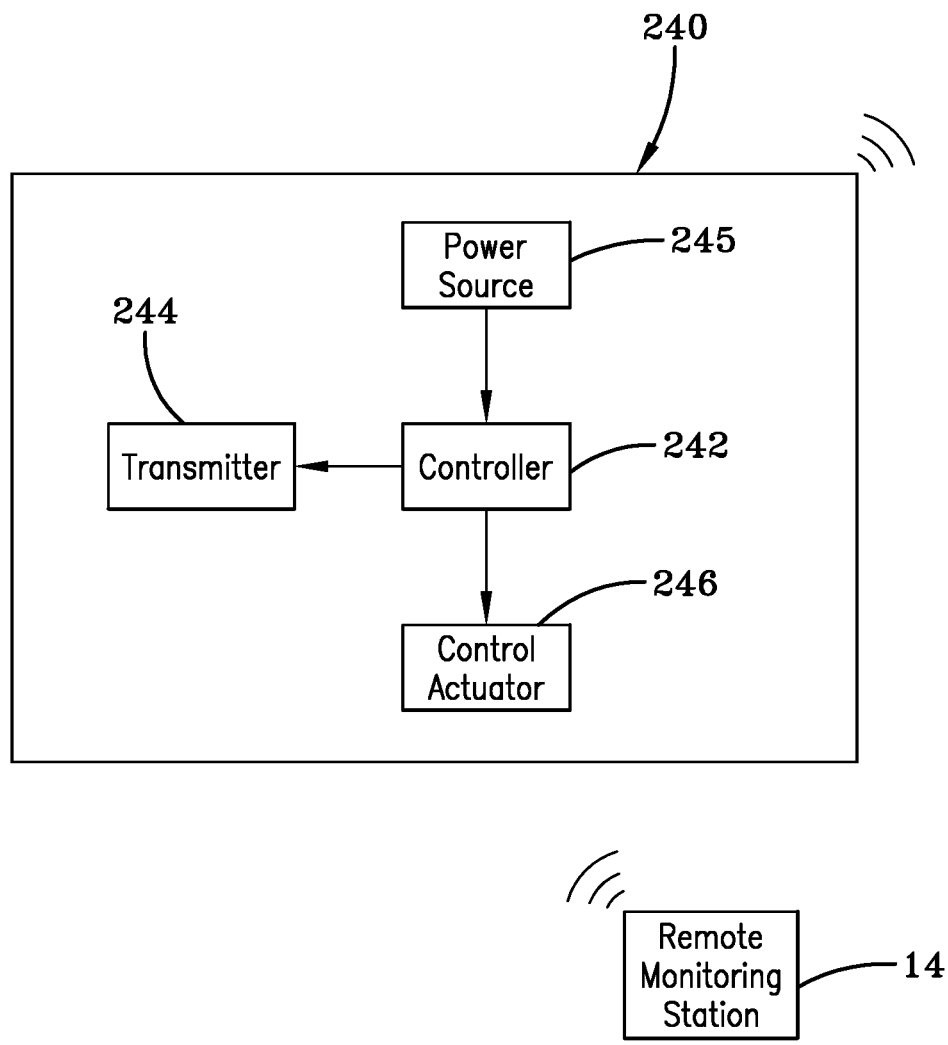
FIG. 7 is a block diagram of another communication module utilized by alternative portable compliance modules in accordance with the concepts of the present invention.

A communication module 240 is embedded within the rear section 220 of the sleeve 200, such that it is adjacent to the rear section 32 of the refill container 20 when the sleeve 200 is installed over the refill container 20. The communication module 240, shown in detail in FIG. 7, includes a controller 242, which has the necessary hardware and/or software that is needed to carryout the functions to be discussed. Coupled to the controller 242 is a wireless transmitter 244 that is configured to transmit a hygiene compliance signal and data to the remote monitoring station 14. In one aspect, the transmitter 244 may comprise a transceiver that is capable of transmitting and receiving data to and from the remote monitoring station 14. The communication module 240 is powered by a power source 245, such as a battery or solar cell for example. A control actuator 246 is coupled to the controller 242 and is configured to extend through an actuator aperture 248 disposed through the rear section 220 of the sleeve 200. However, it is also contemplated that the control actuator 246 may be maintained beneath the rear section 220 of the sleeve 200 as well, so that it is hidden from view. It should be appreciated that the control actuator 246 may comprise a manually-actuated button or switch or may comprise any touch or pressure-sensitive sensor. In one aspect, the control actuator 246 may comprise a biometric sensor that is configured to detect a fingerprint, for example. The communication module 240 is configured to transmit a wireless hygiene compliance signal and data when the control actuator 246 is actuated. Moreover, the communication module 240 is assigned a unique identification code that is associated with the transmitted hygiene compliance signal and data. This allows an administrator of the compliance station 14 to identify and discretely monitor one or more users wearing the compliance module 12B to determine if he or she is in compliance with predetermined hygiene standards and protocols, based on the collected hygiene compliance data.

Disposed about the periphery of the sleeve 200 is a top aperture 260 and two laterally-oriented and opposed shoulder apertures 270A and 270B, which are dimensioned to respectively receive the tab 70 and the shoulders 50A that extend from the refill container 20. As such, when the refill container 20 is received or at least partially received within the sleeve 200, the tab 70 is permitted to extend through the top aperture 260, while the shoulders 50A are dimensioned so that they extend through the shoulder apertures 270A and 270B. As a result, the control actuator 246 is disposed through the actuator aperture 248 in the rear section 220 of the sleeve 200 and is substantially aligned with the dome pump 80 disposed through the receiving aperture 222 in the front section 210 of the sleeve 200.

In order to attach the compliance module 12B to a user or individual, an attachment loop 280 is provided, which extends from the sleeve 200 at a point between the top aperture 260 and the shoulder aperture 270B, although the attachment loop 280 may be provided at any desired position on the sleeve 200.

Thus, during operation of the communication module 12B, the user squeezes or otherwise depresses the dome pump 80, while engaging the control actuator 246 with his or her fingers. The compression of the dome pump 80 dispenses the liquid material from the refill container 20, while the engagement of the control actuator 246 causes the wireless hygiene compliance signal and associated hygiene compliance data to be transmitted from the transmitter 244 to the remote compliance monitoring station 14. The monitoring station 14 records the received compliance signal as a completed hygiene event that is associated with the specific identification code assigned to the specific compliance module 12B. It should be appreciated that the manner of operation of compliance module 12B and the communication module 240 used therewith is equivalent to that of compliance modules 12C-F, which are discussed in detail below.

In yet another embodiment of the portable compliance dispenser 10, a compliance module 12C for use with the refill container 20 is shown in FIGS. 8A-C. Specifically, the control module 12C comprises a body 300 having opposed retention arms 310A and 310B extending therefrom at a substantially right angle, which may comprise any suitable material, such as fabric, including stretchable material, such as neoprene, latex, or the like. In one aspect, the body 300 may have a substantially curved upper edge 320 that terminates at points 322 where each retention arm 310A-B extends from the body 300 at a substantially right angle. The body 300 has opposed inner and outer surfaces 330,332, with a compartment 334 disposed on the outer surface 332. Removably received within the compartment 334 is the communication module 240, as previously discussed, which includes the control actuator 246. It should also be appreciated that the communication module 240 may be carried in a housing, such as an impact-resistant housing, so that it can be readily removed and reinstalled into another compliance module 12C as desired.

The retention arms 310A-B include respective attachment sections 340A and 340B, such that the attachment section 340A is provided on the outer surface 332 of the retention arm 310A, and the attachment section 340B is provided on the inner surface 340 of the retention arm 301B. It should be appreciated that the attachment sections 340A-B may comprise hook and loop material, such as VELCRO®, or any other suitable material or device, such as a snap button, clip, tie, or the like. As such, the arms 310A-B of the body 300 are wrapped around the waist 60 of the body 26 of the refill container 20 and retained thereabout by coupling the attachment sections 340A-B together, such that the control actuator 246 is substantially aligned with the dome pump 80.

To facilitate the attachment of the compliance module 12C to a user, an attachment ring 350 is coupled to the rear surface 332 of the body 300, allowing the compliance module 12C to be removably attached to a belt loop or other item on the user.

Thus during operation of the compliance module 12C, the control actuator 246 is engaged, and the dome pump 80 is depressed, resulting in the liquid material being dispensed from the refill container 20 and the hygiene compliance signal, compliance data, and identification code being transmitted from the remote communication module 240 to the remote monitoring station 14, as discussed with regard to compliance module 12B.

In another embodiment of the portable compliance dispenser 10, a portable compliance module 12D for use with the refill container 20 is shown in FIGS. 9A-C. The portable compliance module 12D includes a body 400 that comprises a retention arm 410 that is coupled to a retention ring 420 by a pair of coupling arches 430. In one aspect, the body 400 may be formed from any suitable material, such as plastic, steel, or aluminum, for example. The compliance module 12D is attached to the refill container 20, so that the retention arm 410 is adjacent to the rear section 32 of the refill container 20 and the retention ring 420 is adjacent to the front section 30 of the refill container 20. Specifically, the compliance module 12D is attached to the refill container 20, whereby a curved gripping section 440 provided by the clip 40 compressively grips the rear section 32 of the refill container 20, while a retention aperture 450 provided by the retention ring 420 receives the dome pump 80 therethrough. To ensure that the compliance module 12D remains in place when attached to the refill container 20, the coupling arches 430 impart a compression force to both the retention arm 410 and the retention ring 420.

Embedded within the retention arm 410 is the communication module 240 previously discussed with regard to compliance module 12B. As such, the control actuator 246 is positioned so as to be substantially aligned with the dome pump 80 when the compliance module 12D is attached to the refill container 20.

Thus, during operation of the compliance module 12D, the dome pump 80 and the control actuator 246 are engaged by the user's hands or fingers to dispense material from the refill container 20. Simultaneously, the communication module 240 wirelessly transmits the hygiene compliance signal, compliance data, and associated unique identification code to the remote monitoring station 14, which records the received compliance signal as a completed hygiene event associated with the unique compliance module identification code.

Figure 10C:
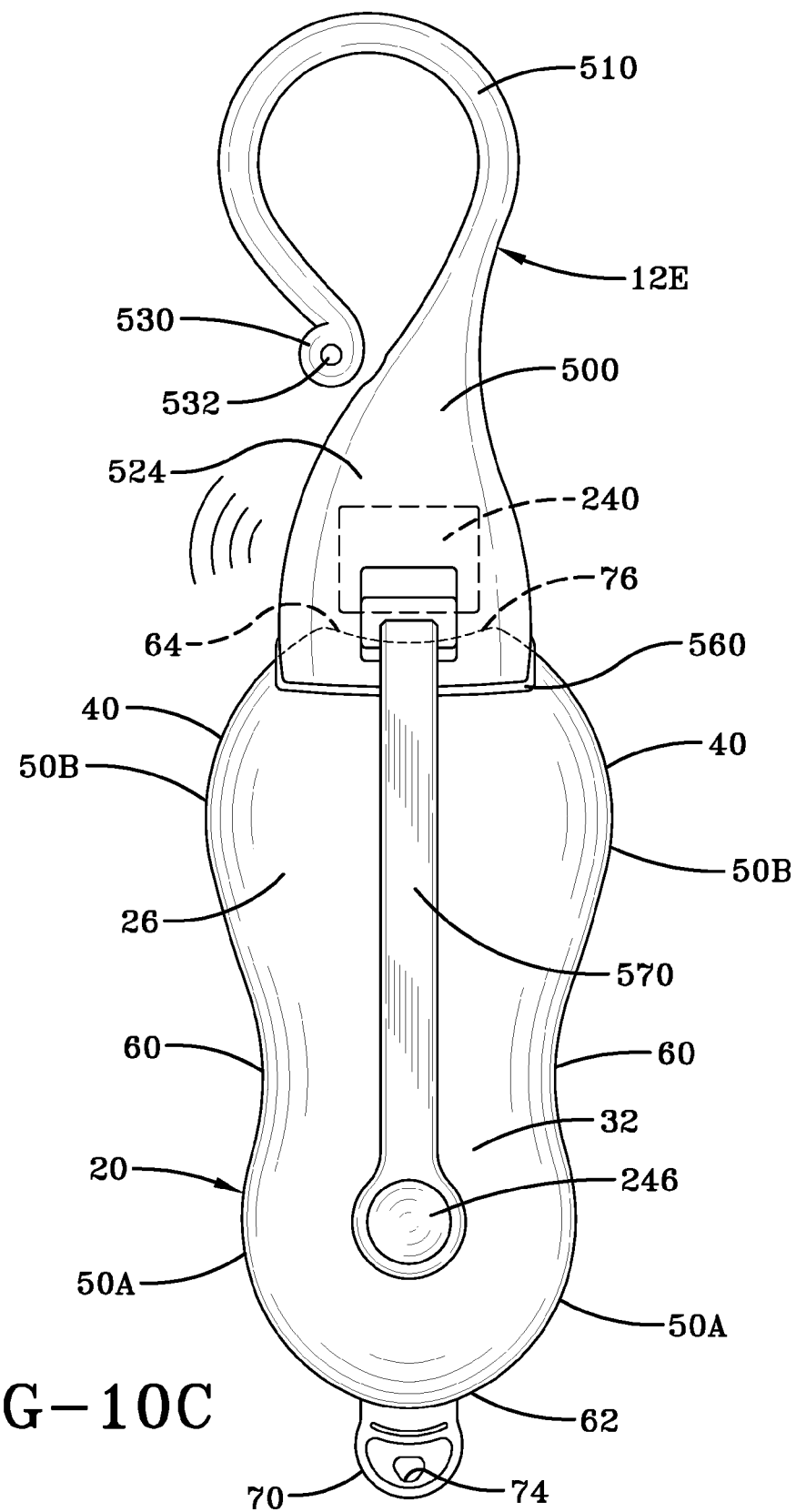
FIG. 10C is a rear elevational view of the portable compliance dispenser of FIG. 10A in accordance with the concepts of the present invention.

In yet another embodiment of the portable compliance dispenser 10, a portable compliance module 12E for use with the refill container 20 is shown in FIGS. 10A-C. The compliance module 12E comprises a substantially elongated body 500 that has a hook 510 at one end and an attachment clamp 520 at its other end. The body 500 has opposed front and rear surfaces 522,524, and may be formed from any suitable material, such as plastic, aluminum, or the like. The hook 510 is dimensioned to attach to any suitable structure, such as a belt loop of a user, for example. The end of the hook 510 also includes a curved end 530 from which extends a lock tab 532. The curved end 530 of the hook 510 is dimensioned to be received and retained within a correspondingly shaped depression 540 disposed in the body 500. To prevent the curved end 530 from inadvertently becoming disengaged from the body 500, the depression 540 includes a lock aperture 542 that is dimensioned to receive the lock tab 532. Thus, when the curved end 530 of the hook 510 is inserted into the depression 540, a closed loop is formed, which secures the compliance module to the user wearing the compliance module 12E.

The attachment clamp 520 includes lock arm 550 that when actuated, opens and closes a pair of substantially parallel and opposed jaws 560 that are configured to compressively engage the attachment section 78, as shown in FIG. 2C, of the refill container 20 that is disposed in the cavity 76. As such, the attachment clamp 520 allows the communication module 12E to be readily removed and attached to the refill container 20 as needed.

Extending from the rear surface 524 of the body 500 is an extension section 570, shown in FIG. 10C, which may be formed of any suitable material such as plastic or metal, which follows the contour of the rear section 32 of the refill container 20. The extension section 570 carries the control actuator 246 that is coupled to the communication module 240 that is disposed within the body 500. Specifically, the control actuator 246 is mounted at a position that is substantially aligned with the dome pump 80 of the attached refill container 20. Thus, when the control actuator 246 and dome pump 80 are engaged, the refill container 20 dispenses the liquid material while the compliance module 12E simultaneously transmits the hygiene compliance signal and data, along with the compliance module identification code, to the monitoring station 14 as previously discussed.

Figures 11A, 11B:
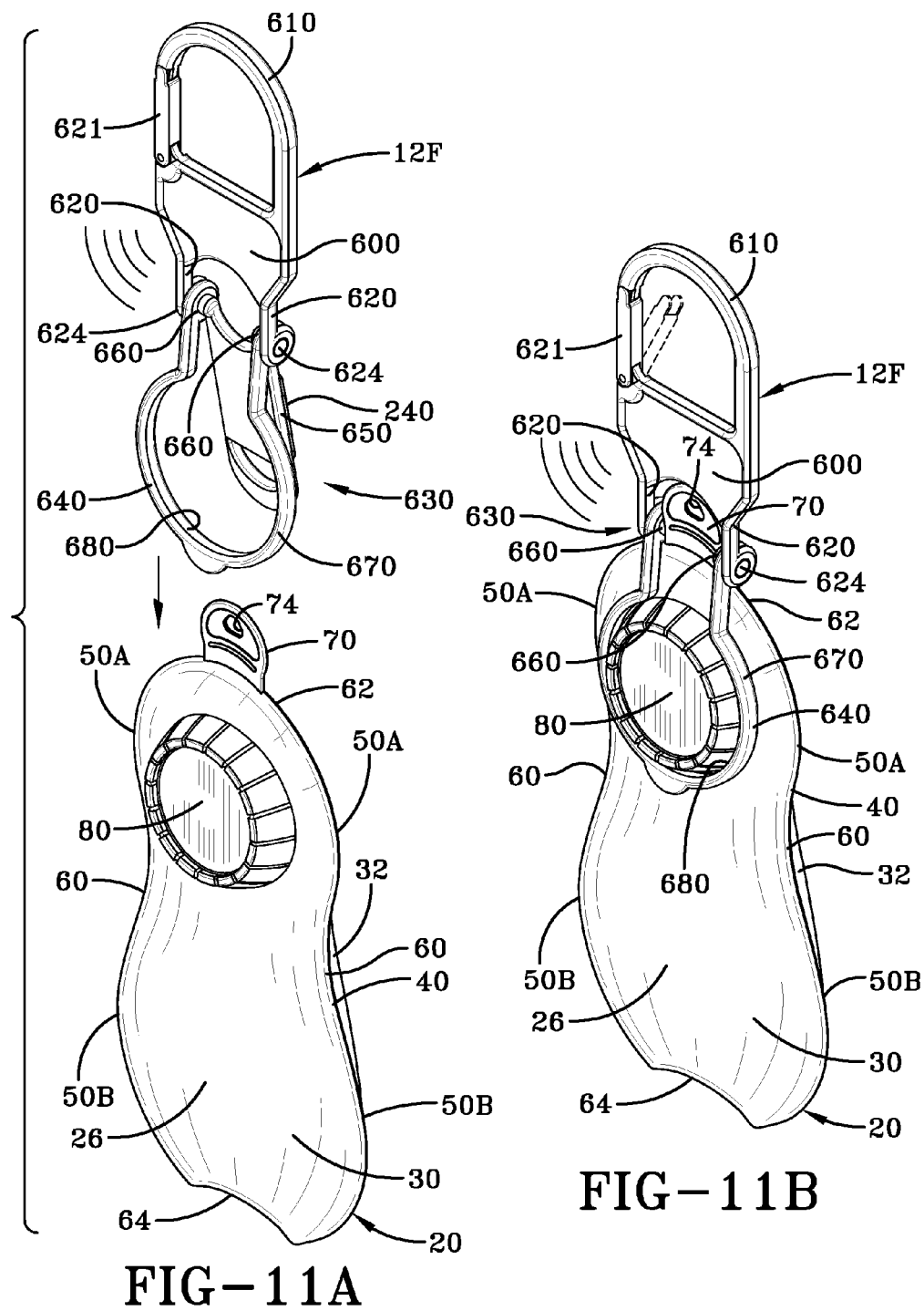
FIG. 11A is a perspective view of an alternate portable compliance dispenser that includes a compliance module that includes a carabiner clip and separated from the refill container in accordance with the concepts of the present invention.
FIG. 11B is a perspective view of the portable compliance dispenser of FIG. 11A attached to the refill container in accordance with the concepts of the present invention.
Figure 11C:
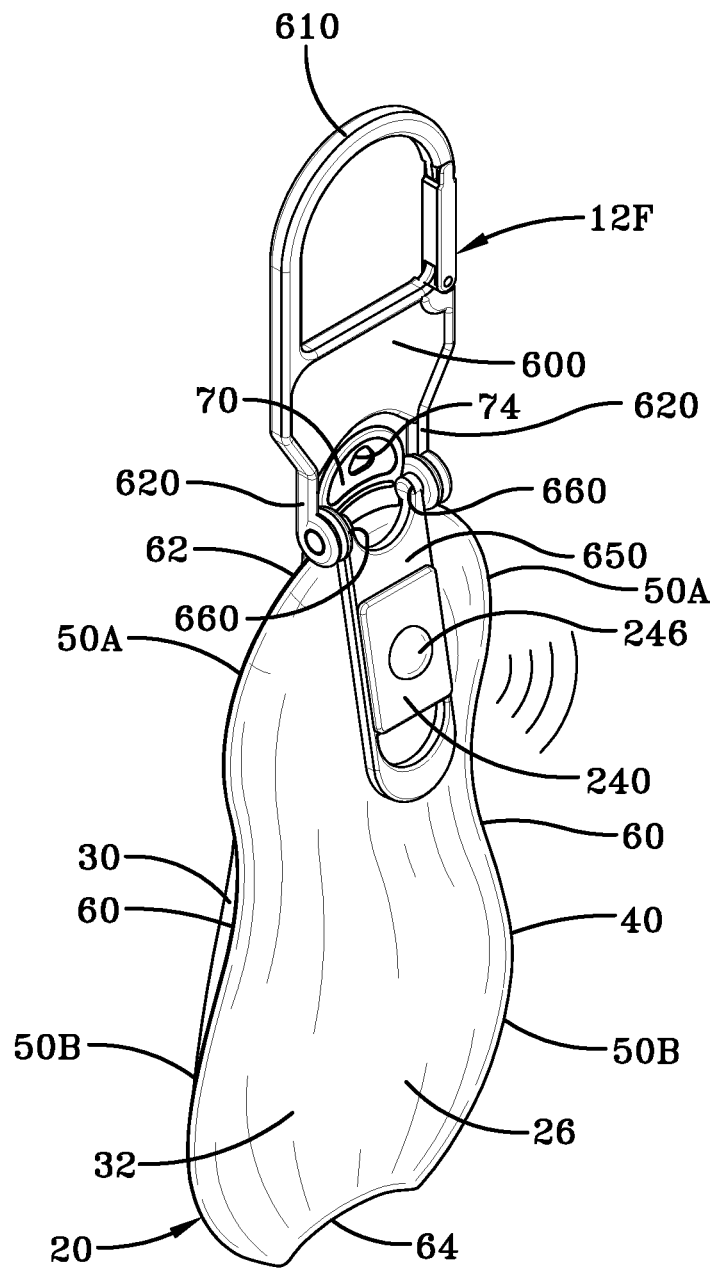
FIG. 11C is a rear perspective view of the portable compliance dispenser of FIG. 11A in accordance with the concepts of the present invention.

In yet another embodiment of the portable compliance dispenser 10, a compliance module 12F for use with the refill container 20 is shown in FIGS. 11A-C. Specifically, the communication module 12F comprises a body 600 from which extends an attachment clip 610, such as a carabiner clip, at one end and a pair of pivot arms 620 at another end. The attachment clip 610 includes a spring-biased closure arm 621, allowing the compliance module 12F to be removably attached to any desired item or structure provided by a user. Pivotably attached to the pivot arms 620 at a pivot point 624 is a mounting clip 630. The mounting clip 630 comprises a lock arm 640 and control arm 650 that extend from each other at an angle at attachment points 660. That is, the lock arm 640 and the control arm 650 comprising the mounting clip 630 are rigidly attached to each other at attachment points 660, while the mounting clip 630 is pivotably attached to the pivot arms 620 that extend from the body 600 at the pivot points 624. In addition, the lock arm 640 includes a retainer 670 that includes a retaining aperture 680 that is dimensioned to receive the dome pump 80 provided by the refill container 20 therethrough.

The compliance module 12F is attached to the refill container 20, such that the lock arm 640 and the control arm 650 are configured to slide over the dispensing end 62 of the refill container 20. During the attachment of the control module 12F to the refill container, the retainer 670 of the lock arm 640 is slid over the dome pump 80, so that it is received within the retaining aperture 680, while the control arm 650 applies a compressive force to the rear section 32 of the refill container 20. It should be appreciated that the dome pump 80 of the refill container 20 may be snap-fit into the retaining aperture 680 of the retainer 670, so as to attach the compliance module 12F to the refill container 20 without the compressive action of the control arm 650. Once the dome pump 80 is received within the retainer 670, the compressive force generated between the lock arm 640 and the control arm 650 is imparted to the refill container 20, thus retaining the compliance module 12F to the refill container 20.

Disposed within the control arm 650 of the compliance module 12F is the communication module 240, as previously discussed. The communication module 240 is configured such that the control actuator 246 is substantially aligned with the dome pump 80 when the compliance module 12F is attached to the refill container 20. This ensures that the control actuator 246 is engaged to denote a completed hygiene event when the dome pump 80 is depressed to dispense liquid material from the refill container 20. Alternatively, the compliance module 12F may be configured, such the pivoting motion of the control arm 650 allows the control actuator 246 to be moved so that it is compressed by the body 600 of the compliance module 12F, thus indicating a completed hygiene event.

Thus, during operation of the compliance module 12F, when the control actuator 246 and the dome pump 80 are depressed, liquid material is dispensed from the refill container 20, and a wireless hygiene compliance signal and data, along with the unique compliance module identification code, are wirelessly transmitted to the remote monitoring system 14, as previously discussed.

Figure 12:
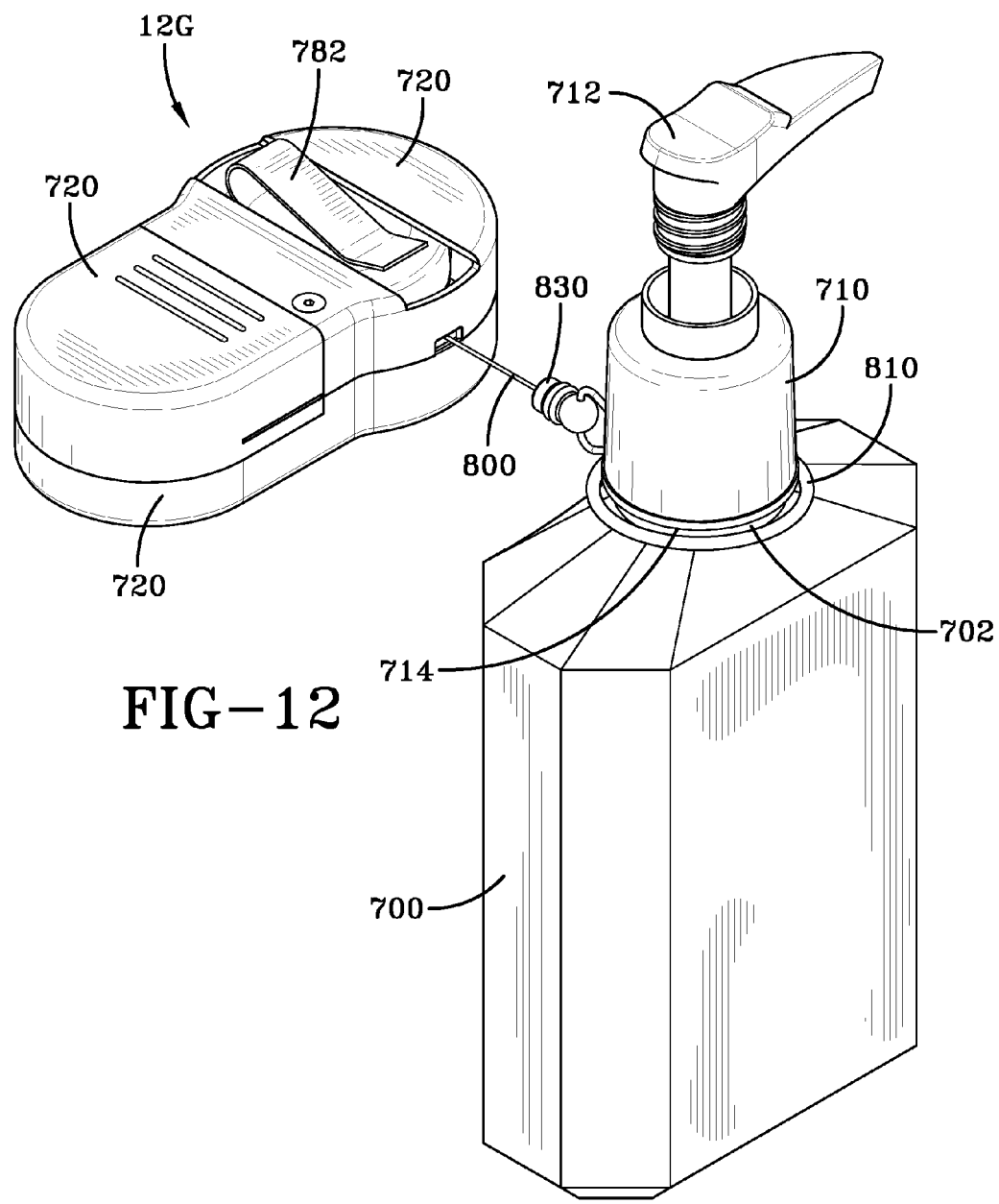
FIG. 12 is a perspective view of another embodiment of a portable compliance dispenser in accordance with the concepts of the present invention.
Figure 13:
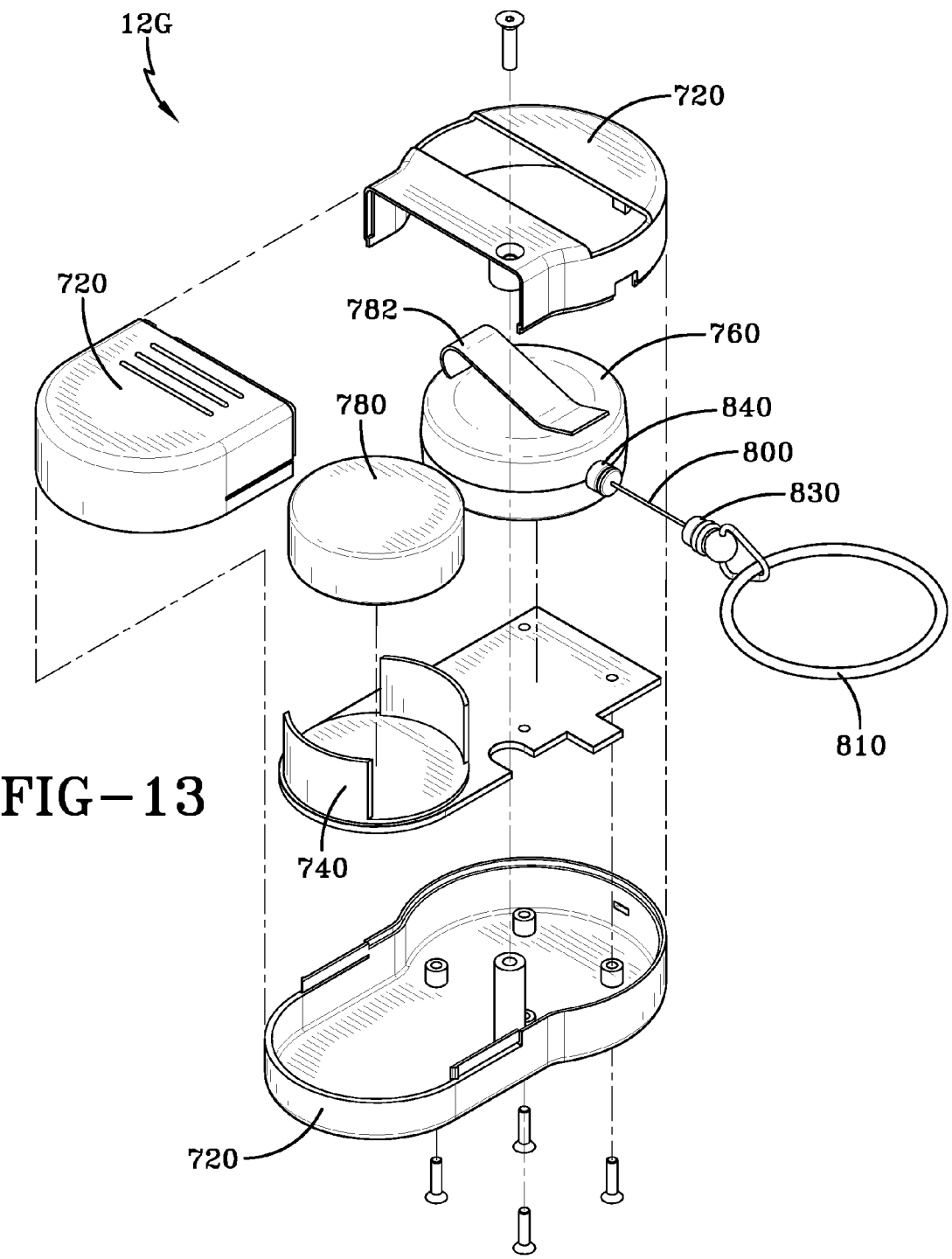
FIG. 13 is an exploded view of the portable compliance dispenser of FIG. 12 in accordance with the concepts of the present invention.
Figure 14:
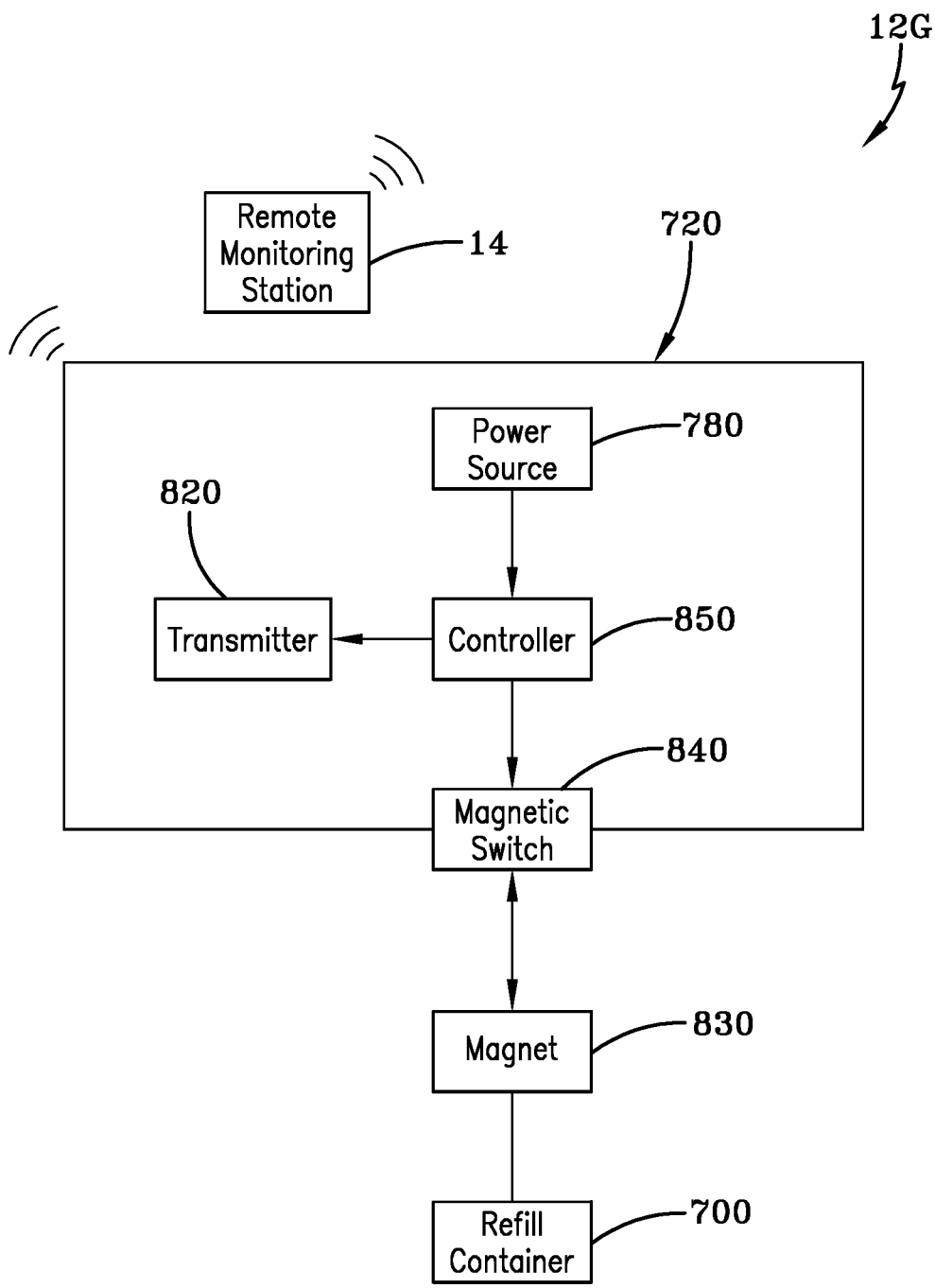
FIG. 14 is a block diagram of the portable compliance dispenser of FIG. 12 in accordance with the concepts of the present invention.

In another embodiment of the portable compliance dispenser 10, a portable compliance module 12G for use with the refill container 20 is shown in FIGS. 12-15. Specifically, the compliance module 12G is configured to be used with a dispensing container 700 having a neck 702 to which an annular collar 710 is threadably attached, as shown in FIG. 12, or other attachment point, such as an attachment aperture for example. The dispensing container 700 includes a pump 712 extending through the collar 710 that when actuated dispenses any suitable liquid material, such as soap or sanitizer for example, therefrom. Specifically, the collar 710 provides an annular collar edge 714 that circumscribes the neck 702 of the dispensing container 700.

The compliance module 12G includes a housing 720 that carries a support member 740 to which a tether retractor 760 and a power source 780, such as a battery, are attached. The housing also includes a carrying clip 782 that is configured to be attached to an individual's belt or other item to allow the compliance module 12G to be worn. The tether retractor 760 is configured to retract a tether 800 that is coupled at one end to the tether retractor 760 and that is coupled at its other end to a retainer 810. The tether 800 may comprise any suitable material as discussed above with regard to tether 114, while the retainer 810 is dimensioned to have a substantially annular shape to allow it to be stretched around the collar 710 so that is retained under its collar edge 714 to thus couple the compliance module 12G to the dispensing container 700. That is, the retainer 810 is made from any suitable stretchable material, such as rubber for example, that allows the retainer 810 to be stretched around the collar 710, whereupon it compresses or constricts about the neck 702 of the dispensing container 700, such that it engages the collar edge 714 of the collar 710. In another aspect, the retainer 810 may comprise a clip or hook that is configured to be attached to the attachment aperture (not shown) provided by the dispensing container 700. It should be appreciated that the tether 800 comprises a retractable cable that is spring biased, or an elastic cord that urges the magnet 830 and the magnetic switch 840 together. The retainer 810 also includes A container magnet 830 attached thereto, the presence of which is detected by a magnetic switch 840 that is carried by the tether retractor 760 to be discussed. In addition, the tether retractor 760 includes a controller 850 that is coupled to the magnetic switch 840, the power source 780, and to a transmitter 870.

Thus, during operation of the compliance module 12G, the dispensing container 700 is fully retracted by the tether 800 so that the presence of the container magnet 830 is magnetically detected by the magnetic switch 840, as shown in FIG. 15A. However, when the user desires to dispense material from the container 700 the container magnet 830 is moved away from the magnetic switch 840, as shown in FIG. 15B. As the magnetic switch 840 detects the removal of the container magnet 830 out of its detection range, the transmitter 870 transmits a wireless hygiene compliance signal or compliance data to the remote monitoring station 14 to indicate that material is being dispensed from the dispensing container 700, and that a hygiene compliance event has occurred. Moreover, when the magnetic switch 840 detects the presence or proximity of the container magnet 830, the controller 850 acknowledges that the dispensing container 700 is not being used to dispense material therefrom and the transmission of the compliance signal or data by the transmitter 870 is terminated.

It will, therefore, be appreciated that one advantage of one or more embodiments of the present invention is that a portable compliance dispenser can be removably coupled to a refill container that contains any liquid material, such as soap, sanitizer, or moisturizer. Another advantage of the present invention is that the portable compliance dispenser is configured to wirelessly transmit hygiene compliance data to monitor the usage of the refill container each time the dispenser is actuated. Still another advantage of the present invention is that the portable compliance dispenser can be easily worn or carried by a user.

Although the present invention has been described in considerable detail with reference to certain embodiments, other embodiments are possible. Therefore, the spirit and scope of the appended claims should not be limited to the description of the embodiments contained herein.

What is claimed is:

1. A portable compliance module for use with a refill container having a pump element to dispense material therefrom when actuated, the portable compliance module comprising:
   a stretchable sleeve adapted to receive at least part of the refill container therein, such that said stretchable sleeve retains the portable compliance module to the refill container; and
   a communication module having a control actuator carried by said stretchable sleeve;
   wherein when said control actuator is actuated, said communication module transmits hygiene compliance data to a remote compliance monitor.

2. The portable compliance module of claim 1, wherein said control actuator is substantially aligned with said pump element of said refill container.

3. The portable compliance module of claim 1, wherein said stretchable sleeve includes a first receiving aperture through which the pump element is accessed.

4. The portable compliance module of claim 1, wherein said control actuator comprises a touch or pressure sensitive sensor.

5. The portable compliance module of claim 1, wherein said control actuator comprises a biometric sensor.

6. The portable compliance module of claim 1, wherein said stretchable sleeve includes one or more retention apertures to receive a portion of the refill container therethrough.

7. The portable compliance module of claim 6, wherein the refill container includes a pair of opposed shoulders that taper to a waist, such that each one of the opposed shoulders are receivable through a respective one of said retention apertures.

8. The portable compliance module of claim 7, wherein said stretchable sleeve extends around the waist of the refill container.

* * * * *